United States Patent [19]

Huck et al.

[11] Patent Number: 4,578,060
[45] Date of Patent: Mar. 25, 1986

[54] WOUND DRAINAGE DEVICE
[75] Inventors: Charles M. Huck, Pottersville, N.J.; Edward W. Larrabee, Bronxville, N.Y.
[73] Assignee: Howmedica, Inc., New York, N.Y.
[21] Appl. No.: 515,504
[22] Filed: Jul. 20, 1983
[51] Int. Cl.[4] .............................. A61M 1/00
[52] U.S. Cl. .................................. 604/133; 604/134
[58] Field of Search .............................. 604/132–135, 604/146, 212–214, 73; 128/760, 765

[56] References Cited

U.S. PATENT DOCUMENTS

| | | | |
|---|---|---|---|
| 799,297 | 9/1905 | Betzler | 401/153 |
| 1,677,603 | 5/1928 | Steen | 222/95 |
| 2,074,223 | 6/1937 | Horiuchi | 128/214 |
| 2,595,493 | 6/1950 | Slaby et al. | 73/425.6 |
| 2,597,059 | 6/1950 | Bitzer | 299/56 |
| 3,084,691 | 9/1963 | Stoner | 128/278 |
| 3,111,145 | 12/1963 | Kerns | 141/26 |
| 3,115,138 | 1/1964 | McElvenny et al. | 128/278 |
| 3,376,868 | 4/1968 | Mondiadis | 128/278 |
| 3,416,431 | 12/1968 | Hitzeroth | 99/391 |
| 3,421,662 | 1/1969 | Hanson | 222/95 |
| 3,556,101 | 1/1971 | Economou | 128/277 |
| 3,654,964 | 4/1972 | Mercier | 138/30 |
| 3,680,560 | 8/1972 | Pannier et al. | 128/276 |
| 3,742,952 | 7/1973 | Magers | 128/278 |
| 3,774,611 | 11/1973 | Tusey et al. | 128/278 |
| 3,779,243 | 12/1973 | Tusey et al. | 128/278 |
| 3,809,086 | 5/1974 | Schachet | 128/278 |
| 3,809,087 | 5/1974 | Lewis, Jr. | 128/278 |
| 3,843,016 | 10/1974 | Bornhorst et al. | 220/306 |
| 3,845,765 | 11/1974 | Ideda | 128/277 |
| 3,871,554 | 3/1975 | Huck | 222/96 |
| 3,875,941 | 4/1975 | Adair | 128/278 |
| 3,889,677 | 6/1975 | Nehring | 128/278 |
| 3,911,920 | 10/1975 | Susinn | 128/281 |
| 3,931,834 | 1/1976 | Caillet | 128/281.2 |
| 3,945,392 | 3/1976 | Deaton et al. | 137/205 |
| 3,965,902 | 6/1976 | Reilly et al. | 128/276 |
| 3,989,046 | 11/1976 | Pannier, Jr. et al. | 128/276 |
| 4,013,076 | 3/1977 | Puderbaugh | 128/276 |
| 4,022,209 | 5/1977 | Nehring | 128/278 |
| 4,058,123 | 11/1977 | May | 128/278 |
| 4,073,294 | 2/1978 | Stanley et al. | 128/278 |
| 4,085,751 | 5/1978 | Dodge | 128/275 |
| 4,111,204 | 9/1978 | Hessel | 128/276 |
| 4,112,947 | 9/1978 | Nehring | 128/278 |
| 4,136,802 | 1/1979 | Mascia et al. | 222/95 |
| 4,141,361 | 2/1979 | Snyder | 604/133 X |
| 4,278,089 | 7/1981 | Huck et al. | 604/134 |

FOREIGN PATENT DOCUMENTS

| | | |
|---|---|---|
| 879849 | 2/1973 | Canada . |
| 1282856 | 11/1968 | Fed. Rep. of Germany . |
| 1810801 | 3/1970 | Fed. Rep. of Germany . |
| 1239249 | 2/1960 | France . |
| 53196 | 3/1982 | Japan . |
| 939529 | 5/1963 | United Kingdom . |
| 1304324 | 7/1972 | United Kingdom . |
| 1395799 | 12/1974 | United Kingdom . |
| 1400139 | 2/1975 | United Kingdom . |
| 1404959 | 10/1975 | United Kingdom . |
| 1435771 | 5/1976 | United Kingdom . |
| 1435772 | 5/1976 | United Kingdom . |
| 1480144 | 3/1977 | United Kingdom . |
| 1485279 | 10/1977 | United Kingdom . |
| 1524375 | 4/1980 | United Kingdom . |
| 2039745 | 8/1980 | United Kingdom . |

OTHER PUBLICATIONS

"Bellows" Websters Seventh New Collegiate Dictionary GC Thomson Co. Springfield, Mass. 1963, p. 79.

*Primary Examiner*—Dalton L. Truluck
*Attorney, Agent, or Firm*—Pennie & Edmonds

[57] ABSTRACT

A device for removing fluids from a wound includes a housing and a resilient bellows inside the housing. The bellows can be collapsed and retained in a collapsed or activated state. Upon release from its activated state, the bellows is expanded so as to create a negative pressure therein whereupon fluids are automatically drawn into and collected within the bellows. Preferably the bellows is expanded by a variable force ribbon spring so that the resultant or combined restoring force provided by the resilient bellows and the variable force ribbon spring allows for the creation of a substantially constant level of negative pressure within the bellows so as to provide for a substantially constant level of suction of the device throughout the range of evacuation of fluids therein. The housing is preferably transparent with graduations provided thereon permitting the visible inspection and measurement of the fluids collected therein. A method for operating the device is also disclosed.

27 Claims, 9 Drawing Figures

WOUND DRAINAGE DEVICE

TECHNICAL FIELD

This invention relates to suction devices and more particularly to an improved device for automatic removal of fluids from a wound.

BACKGROUND ART

The use of suction devices to remove fluids from a wound is known to the art. Such devices are employed to reduce or remove the body fluids which normally collect at a wound site after surgery.

Body fluids which collect at a wound, if left to remain especially in a closed wound, may cause complications in the healing process and thereby reduce the chance of a successful convalescence. Moreover, not only will a dry wound area accelerate the healing stage but will also promote cicatrization.

Known typical suction devices are both disclosed and illustrated in Canadian Pat. No. 879,849; British Pat. Nos. 1,304,324 and 1,400,139; and U.S. Pat. Nos. 3,115,138; 3,376,868; 3,742,952; 3,774,611; 3,779,243; 3,809,086; 3,809,087; and 3,875,941.

Canadian Pat. No. 879,849 discloses a device which includes a container with a concertina-pleated wall that can be expanded to increase the volume of the container. A detachable external spring bow serves to extend the pleated wall thereby causing suction within the container. The concertina-pleated walls are consecutively numbered to permit measurement of the fluid collected when the container is in an open extended position.

British Pat. No. 1,304,324 discloses a bellows operated disposable aspiration drainage device. A nonreturn inlet valve permits the collection of body fluids into the bellows from an inlet catheter connected to the wound to be drained. The collected body fluids are discharged through a non-return outlet valve into a receiving bag. The latter is graduated to allow measurement of removed body fluids.

British Pat. No. 1,400,139 discloses a suction drainage device which includes a resiliently compressible, airtight container having a watertight plastic bag detachably secured therein. The container upon expansion produces a negative pressure which results in the flow of body fluids into the bag within. A helical spring can be used inside the container to provide expansion of the container.

U.S. Pat. No. 3,115,138 discloses an evacuator that includes a fluid tight container. After manual compression, the container is expandable to provide suction either by means of internally positioned springs between additional members placed within the container or by virtue of the container being constructed of resilient material The evacuator disclosed in U.S. Pat. No. 3,376,868 includes a compressible container made from resilient elastomeric material whose memory causes the walls to return to an uncompressed state. A valve turret on the top of the container provides both an inlet and a vent opening which is sealable by means such as a plug or a resilient diaphragm connected to the top.

U.S. Pat. No. 3,742,952 discloses a surgical suction assembly including a suction container which is resiliently compressible and expandable. A one way plug is provided to admit fuild into the container while drawing fuild and to block flow outwardly therefrom.

U.S. Pat. No. 3,774,611 discloses a contamination free evacuator including a compressible-expandable container having an inlet and an outlet region, and a fluid stabilizer inside the container.

A contamination free evacuator is also disclosed in U.S. Pat. No. 3,779,243 which includes a compressible and expandable evacuator bag having both a drain inlet and an exhaust outlet fromed in the bag. The latter further includes a magnetic one-way exhaust valve which prevents the contamination of the bag by closing upon completion of exhausting fluids from the bag.

U.S Pat. No. 3,809,086 is directed to a wound suction device including a vessel having therein an elastic sheet diaphragm which is sealed to the walls of the vessel. Movement of the diaphragm by a plate with an actuating means decreases the volume of the vessel which results in the creation of a suction force upon release of the actuating means. Provision is made to lock the actuator means in a position such that the resilient diaphragm remains displaced.

In U.S. Pat. No. 3,809,087, a suction apparatus is disclosed having a collapsible bag attached at opposed surfaces to plate members one of which is biased to move away from the other plate member. Disclosed biasing means include springs and rubber bands.

The evacuating system disclosed in U.S. Pat. No. 3,875,941 includes a bellows-type container having resilient accordian-like sidewalls made of an elastomeric material. Initial suction of the container is provided by the resilient accordian-like sidewalls. Further suction results from the added weight of collected fluid within the container. Operation of this system requires that the bellows-type container be mounted in a vertical position with evacuating tubing attached to the top portion of the container.

Although each of the above-mentioned patented devices is useful in varying degrees, they all suffer from some of several disadvantages which include, e.g., the necessity of activation just prior to use, the lack of ease in operation, the need for a specific orientation during operation, complex structure, and the inability to maintain a substantially constant level of negative pressure.

All of the above patents except U.S. Pat. No. 3,809,086 provide no disclosure of a device which can be received by the handler in a preactivated or compressed state. These devices require that the handler collapse the bellows or container to activate the device before use. Difficulty in operation is presented particularly in the devices of British Pat. No. 1,304,324; Canadian Pat. No. 879,849; and U.S. Pat. No. 3,875,941. Moreover, British Pat. No. 1,304,324 discloses a directional multicomponent valve system which requires that the handler properly connect the device to the wound and the collecting bag. Multi-component complex valve arrangements are also disclosed in U.S. Pat. Nos. 3,742,952 and 3,779,243. Canadian Pat. No. 879,849 not only requires that the user compress the concertina-pleated walls to drain air from the device but also requires attachment of an external spring bow thus further complicating the operation thereof. In the device of U.S. Pat. No. 3,875,941, difficulty arises from the requirement that the device be maintained upright for proper operation, i.e., it is orientation sensitive. Increased cost of operation or construction results from the multi-component or complex valve systems disclosed in British Pat. No. 1,304,324 and U.S. Pat. Nos.

3,742,952 and 3,779,243; and from the need of additional collecting bags in British Pat. Nos. 1,304,324 and 1,400,139. Complex structure is formed in the multiple spring arrangement disclosures of U.S. Pat. Nos. 3,115,138; 3,779,243 and 3,809,087; and in the need of a fluid stabilizer as disclosed in U.S. Pat. No. 3,774,611. Such complex structures, as noted above, complicate construction as well as increase the cost thereof. In addition, none of the above-listed patents disclose a device which provides substantially constant suction over the range of operation.

We have invented an improved suction device which is intended to improve over the structures discussed above and to overcome the limitations found therein. The device of the present invention is designed to provide a substantially constant negative pressure throughout the range of drawing and collecting body fluids from a wound into the device. Also the device is available to the user in a preactivated state. The device thus avoids the need for the handler to discharge the air within the device as is found to be the case with almost all of the apparatus of the above discussed prior art. Additional ease of operation is provided herein in that this device permits one hand operation freeing the handler to attend to additional matters while simultaneously activating the device. The device is also designed to permit alternatively either total discard or evacuation of the collected fluids and reactivation for subsequent reuse.

DISCLOSURE OF INVENTION

The present invention relates to a device for drawing fluids therein comprising a housing having an end wall and an opening therein, an airtight and watertight resilient container disposed within the housing and being collapsible and expandable therein, means for communicating with the interior of the container, means for collapsing the container within the housing, and variable force means for automatically expanding the container from its collapsed state such that the combined resultant force of the variable forces provided by the container and the variable force expansion means allows for the creation of a substantially constant level of negative pressure within the container so as to provide for the drawing of fluids therein at a substantially constant level of suction.

In a preferred embodiment, the device comprises an elongated housing having at least one end wall at one end thereof, said end wall having an opening, an airtight and watertight resilient elongated bellows disposed within the housing, the bellows being collapsible and expandable and having an upper and a lower end, means for communicating with the interior of the bellows, means for maintaining the upper end of the bellows adjacent said end wall of the housing, means for collapsing the bellows within the housing, and variable force means for automatically expanding the bellows from its collapsed state such that the combined resultant force of the variable forces provided by the bellows and the variable force expansion means allows for the creation of a substantially constant level of negative pressure within the bellows so as to provide for the removal of fluids from the wound at a substantially constant level of suction substantially throughout the range of evacuation.

Preferably the variable force expansion means is a variable force spring assembly. The device further comprises means for retaining the bellows in a collapsed state. A base is attached to the other end of the housing and one end of the variable force spring assembly is secured within the base. The housing has a generally cylindrical side wall which includes at least one slit aligned with the longitudinal axis of the housing. The slit extends from a first position spaced from the end wall to a second position spaced from the other end of the housing.

The collapsing means comprises a disc-shaped collar slidably engaged within the housing between the other end of the housing and the lower end of the bellows and secured to the other end of the variable force spring assembly. The collar is also attached to the lower end of the bellows and has at least one tab extending radially therefrom. The tab is slidably engaged within and extends beyond the slit. Movement of the tab toward the first position collapses the bellows.

The first position is suitably chosen so that the bellows is substantially fully collapsed when the tab is at the first position.

The retaining means comprises at least one cutout positioned at the first position and communicating with the slit. The cutout is suitably dimensioned and configured so as to receive the tab when the tab is at the first position and twisted into the cutout. In this fashion, the cutout holds the tab and thereby retains the bellows in a collapsed state.

The variable force spring assembly preferably is a ribbon spring having a free end extending along the longitudinal axis of the housing and being attached to the bellows. Release of the tab from its respective cutout allows the ribbon spring to draw the collar toward the other end of the housing so as to expand the bellows and produce a negative pressure therein. The ribbon spring, e.g., a negator spring, is programmed so that its restoring force combined with that of the bellows provides a substantially constant force of suction of fluid into the bellows.

Preferably the housing is substantially rigid and is formed of a transparent plastic so as to permit visible inspection of the operation of the bellows, the collar, and the ribbon spring within the housing. Also, the bellows is formed of a transparent plastic so as to permit visible inspection of the fluid withdrawn therein from the wound. Graduations are provided on the housing so as to permit the measurement of fluid withdrawn therein from the wound. In addition, textured, e.g., frosted predetermined areas are provided on the housing to permit selective imprinting of desired information thereon.

The communicating means includes a hollow tube which is integral with the upper end of the bellows. The tube extends through the opening of the end wall such that the interior of the bellows is in communication with the outside of the housing. The maintaining means includes a partial flange disposed on the hollow tube and above the upper end of the bellows a distance at least slightly larger than the thickness of the end wall. In this fashion the flange is adapted to normally permit one-way passage of the hollow tube from within to without the housing through the opening of the end wall such that the upper end of the bellows is maintained adjacent the end wall of the housing.

Alternatively, the bellows includes an integral member extending outwardly from the end wall of the housing. The integral member is dimensioned and configured so as to pass through the second opening out from the housing such that the upper end of the bellows is maintained in a secured relationship with the end wall of the housing.

Means are also provided, preferably in the form of a strap passing through a C-clip on the housing for portably supporting same on the body as a self-contained portable unit.

The present invention is also directed to a method for drawing fluids from a portion of a body comprising taking a suction device in a preactivated state, the device including a housing having at least one opening, airtight and watertight resilient container means disposed within the housing, the resilient container means being collapsible and expandable and having its interior in communication with the opening in the housing, and variable force expansion means disposed outside the resilient container means and secured to the housing for automatically expanding the resilient container means from at least a partially collapsed state such that the combined resultant force of the variable forces provided by the resilient container means and the variable force expansion means allows for the creation of a substantially constant level of negative pressure within the resilient container means so as to provide for the drawing of fluids therein from a portion of a body at a substantially constant level of suction substantially throughout the range of evacuation, connecting the opening of the housing to a portion of a body from which fluids are to be drawn, and activating the suction device so as to draw fluids into the suction device at a substantially constant rate of suction. If desired, the device can be portably supported from the body.

BRIEF DESCRIPTION OF DRAWINGS

The present invention is described in greater detail hereinbelow, with reference to the drawings wherein.

BEST MODE FOR CARRYING OUT THE INVENTION

In the description which follows, any reference to either orientation or direction is intended primarily and solely for the purpose of illustration and is not intended in any way as a limitation of the scope of the present invention or the claims thereto. Also, the particular embodiments described herein although being preferred are not to be considered as limiting of the present invention. Furthermore, like parts or elements in the various drawings hereto are identified by like numerals.

Figure 1:
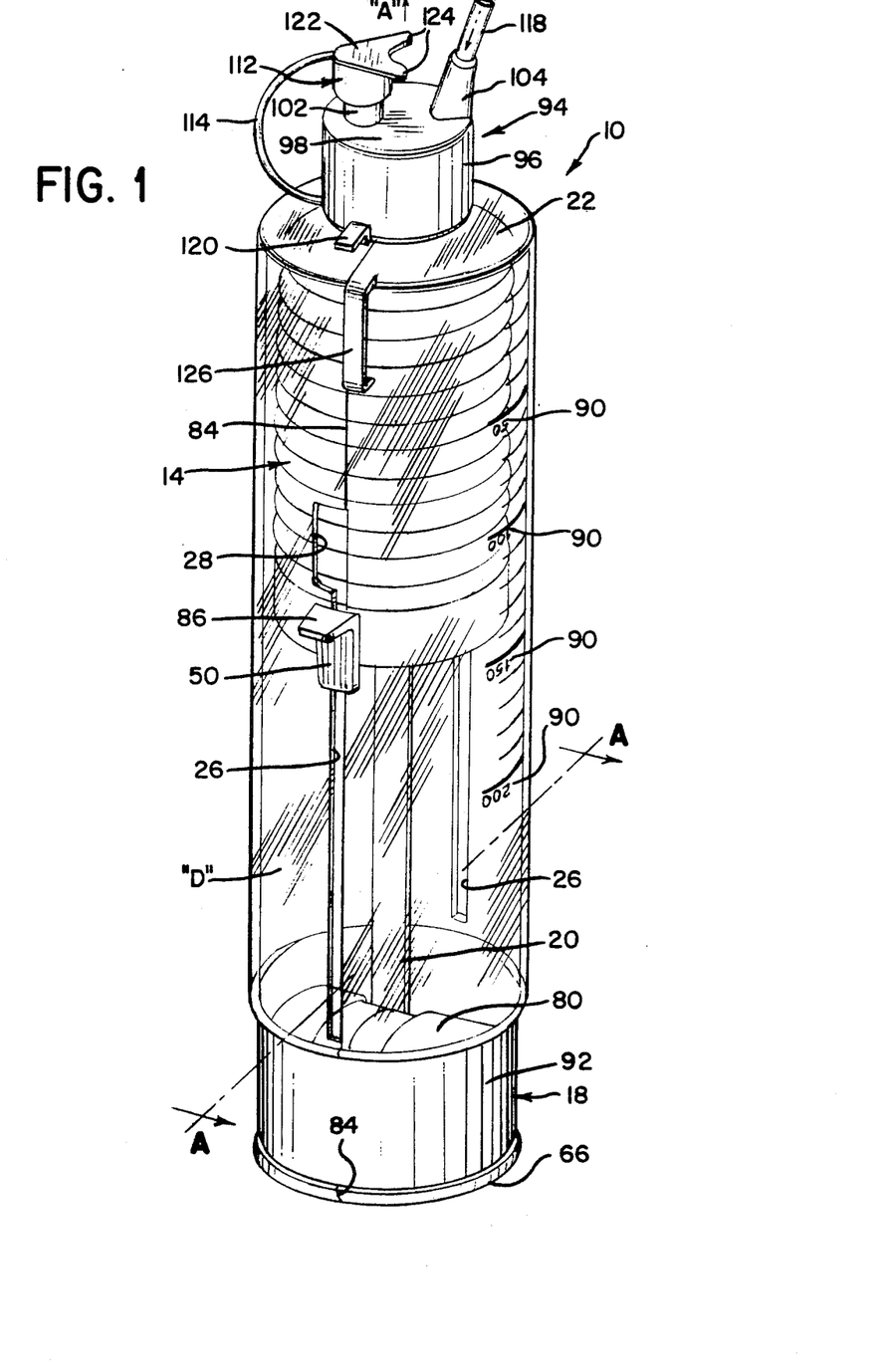
FIG. 1 is a prespective view of a wound drainage device according to the present invention.

The suction device 10 according to the present invention is illustrated in FIG. 1 in an operative mode of drawing fluids, e.g., from a portion of a body (not shown) in the direction of the arrows indicated thereon.

Figure 2:
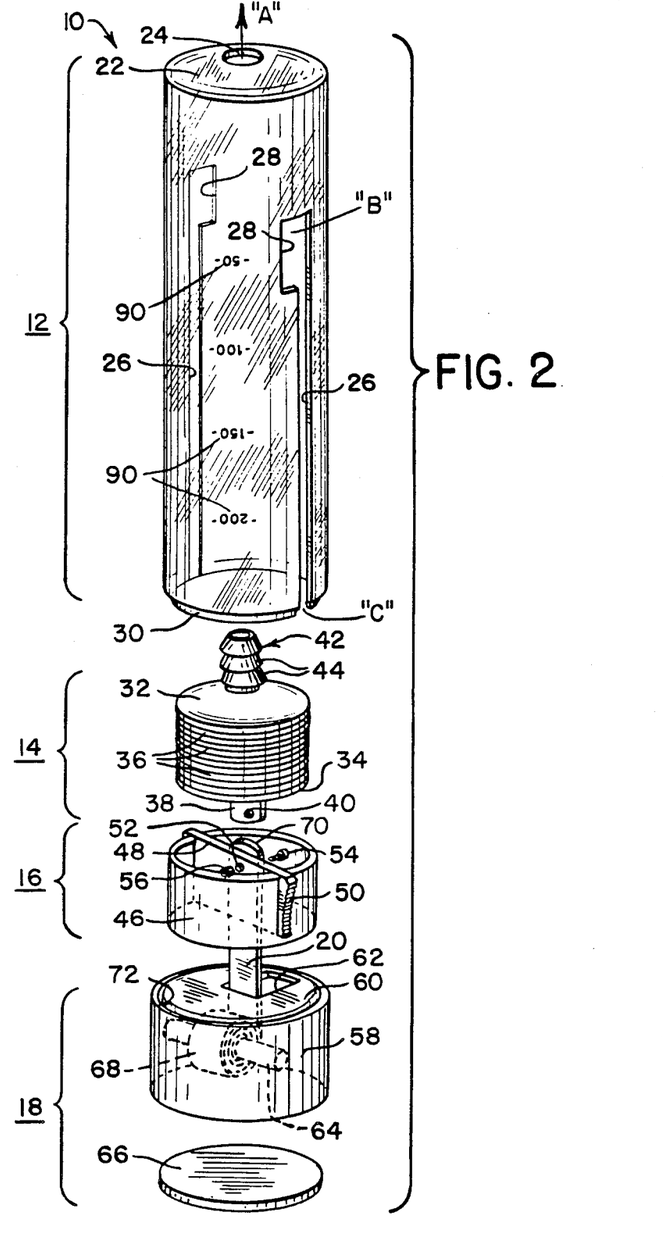
FIG. 2 is an exploded view of an alternative embodiment of the device of FIG. 1.

FIG. 2 provides an exploded view of an alternative embodiment of the suction device 10 according to the present invention thereby illustrating the component parts and structure as well as the assembly thereof. Generally the device 10 comprises a substantially rigid cylindrical housing 12 closed at the upper end and open at the lower end, and enclosing in sequence from the closed end a container, e.g., a resilient bellows 14, a slide collar 16, and a base 18 which is securely mated to the open end of the housing 12. A variable force spring assembly 20 is housed within the base 18. Both the spring assembly 20 and the bellows 14 are attached to the slide collar 16. In operation, as shown in FIG. 1, the bellows 14 is expanded or kept constantly expanding by the combined restoring resultant force provided by the complementary variable forces of both the resilient bellows 14 and the spring assembly 20.

The housing 12 of the device 10 has an integral end wall 22 at the closed end thereof. The end wall 22 has an opening 24 which permits communication with the bellows 14 within the housing 12. Two slits 26 are oppositely positioned in the side walls of the housing 12 and are substantially aligned with the longitudinal axis of the housing 12 as indicated by the arrow "A" in FIG. 2. The slits 26 run from a first position to a second position, identified in FIG. 2 by letters B and C, respectively, the latter being coincident with the lower end of the housing 12. The slits 26 at the first position include cutouts 28 as shown in FIGS. 1 and 2. The purpose of slits 26 and cutouts 28 will be more fully described hereinbelow. The lower end of the housing 12 in the alternative embodiment illustrated in FIG. 2 terminates integrally in a ring 30 which has an outside diameter less than the outside diameter of the housing 12.

The bellows 14 has an upper end 32 and a lower end 34 and is positioned within the housing 12 with its upper end 32 adjacent the end wall 22. The bellows 14 has ribbed portions 36 which permit the bellows 14 to expand so as to increase its volumetric capacity. At the lower end 34 of the bellows 14 is an appendage 38 with opening 40 therein which, as will be described hereinbelow, permits coupling of the bellows 14 with the remaining structure within the housing 12. Integral with the upper end 32 and communicating with the interior of the bellows 14 is a tube 42. The tube 42 has circumferentially thereon three flanges 44 each having a frusto-conical shape which permits passage of the tube 42 through the end wall opening 24. The bottommost flange is positioned above the upper end 32 of bellows 14 a distance at least slightly larger than the thickness of end wall 22. Hence, the bottommost flange after passing through hole 24 rests against the upper surface of end wall 22 and does not allow the tube 42 to be withdrawn back through the opening 24. In this manner the upper end 32 of the bellows 14 is kept adjacent the end wall 22. The bellows 14 can then be expanded downward toward the lower end of the housing 12.

Also enclosed within the housing 12 is a slide collar 16 which includes an annular collar ring 46 that slides within the housing 12. The longitudinal axis of ring 46 is aligned with that of the housing 12. The slide collar 16 also includes a cross bar 48 which is positioned along one diameter of the collar ring 46 in slots (not shown separately) and extends beyond that one diameter to oppositely positioned tabs 50. When engaged within the slits 26 the tabs 50 protrude beyond the side walls of the housing 12. The tabs 50 are shaved at an angle toward the base 18 and are ribbed as well so that they may be easily engaged by the user's fingers. The cross bar 48 also has a first opening 52 by means of which the bellows 14 can be attached to the slide collar 16. After aligning opening 40 of the bellows 14 with opening 52, a bolt 54 can be passed through bellows opening 40 and cross bar opening 52. A nut 56 is threaded onto the free end of bolt 54 thereby securing bellows 14 to the slide collar 16.

The base 18 comprises a generally cylindrical base ring 58 with an integral top end wall 60. The top end wall 60 has a generally rectangular opening 62. A pin 64 is positioned along a chordal length of base ring 58 and secured to the inside walls thereof as shown more clearly in FIG. 2. A bottom end wall 66 seals the base 18.

The spring assembly 20 is formed of a coiled spring portion 68 and an uncoiled free portion 70. The coiled spring portion 68 is housed within the base 18 and coiled about post 64. The uncoiled or free portion 70 extends through opening 62 of the top end wall 60 and has an opening (not shown) which permits the attachment of the spring assembly 20 to the slide collar 16 after alignment with the opening 52 of the cross bar 48 via the bolt 54 and nut 56 in the same manner that the bellows 14 is attached to the collar 46. The top end wall 60 has circumferentially within its upper edge a groove 72 configured in shape and size to matably receive the housing ring 30.

Figure 4:
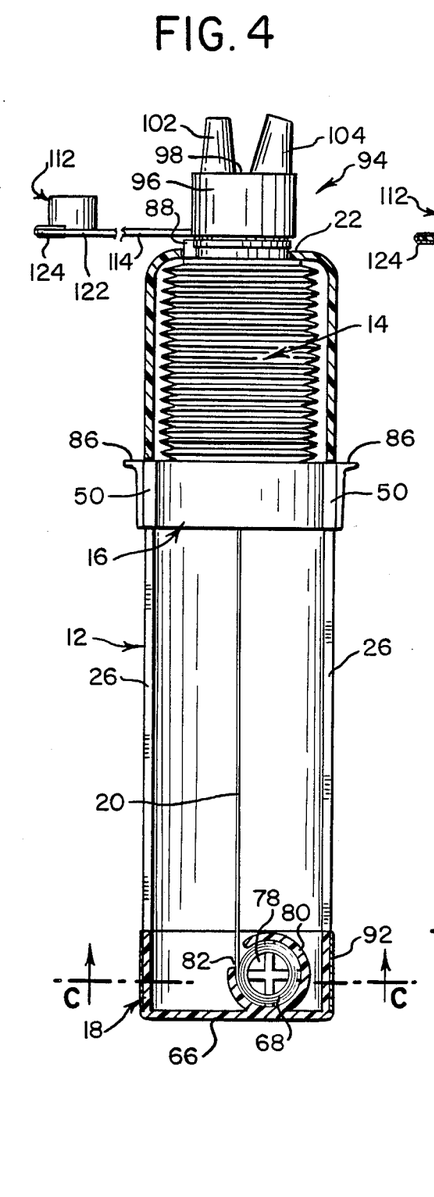
FIG. 4 is a side elevational view of the device of FIG. 1 taken in the direction of lines A—A of FIG. 1.

After the bellows 12 and base 18 are each attached as described above to the slide collar 16, assembly of the device 10 is accomplished by inserting the above-mentioned components bellows 14 first through the open end of housing 12 so that the tabs 50 are slidably engaged within slits 26. The bellows 14 is inserted tube 42 first. Once the bottommost flange of the tube 42 passes through the end wall opening 24, the tube 42 cannot pass back into the housing 12. In addition, the upper end of the bellows 14 is thereby kept adjacent the cover 22 and thus serves as a fixed point from which the bellows 14 can expand by means of the force of spring assembly 20 combined with the restoring force of the resilient bellows 14 itself. Assembly is completed when the base 18 is secured to the housing 12 by means of fitting housing ring 30 into base groove 72. When the tabs 50 are advanced to the first position ("B") or slide into the housing 12 as far as possible, a slight twisting of the tabs 50 into the cutouts 28, dimensioned so as to receive the tabs 50 as shown in FIG. 2, will lock the tabs 50 in place. In this fashion, the bellows 14 will be compressed or collapsed as shown in FIG. 4. The first position ("B") of the slits 26 is preferably chosen so that the bellows 14 is fully collapsed when the tabs 50 are engaged within the cutouts 28. Upon release of the tabs 50 from their locked positions within cutouts 28, the combined restoring resultant force of the bellows 14 and variable force spring assembly 20 will automatically draw the slide collar 16, without further action on the part of the user, toward the lower end of the housing 12 and will simultaneously automatically expand the bellows 14 which is attached to the slide collar 16 thereby producing a substantially constant negative pressure within the bellows 14. In this fashion, fluids can be drawn into the bellows 14 at a constant level of suction.

FIG. 4 particularly illustrates the positions of the component structures of the device 10 when the bellows 14 is in a collapsed or preactivated state within the housing 12. Upon completely withdrawing fluids into the bellows 14, the structure of the device 10 assumes the configuration shown in FIG. 5.

Figure 5:
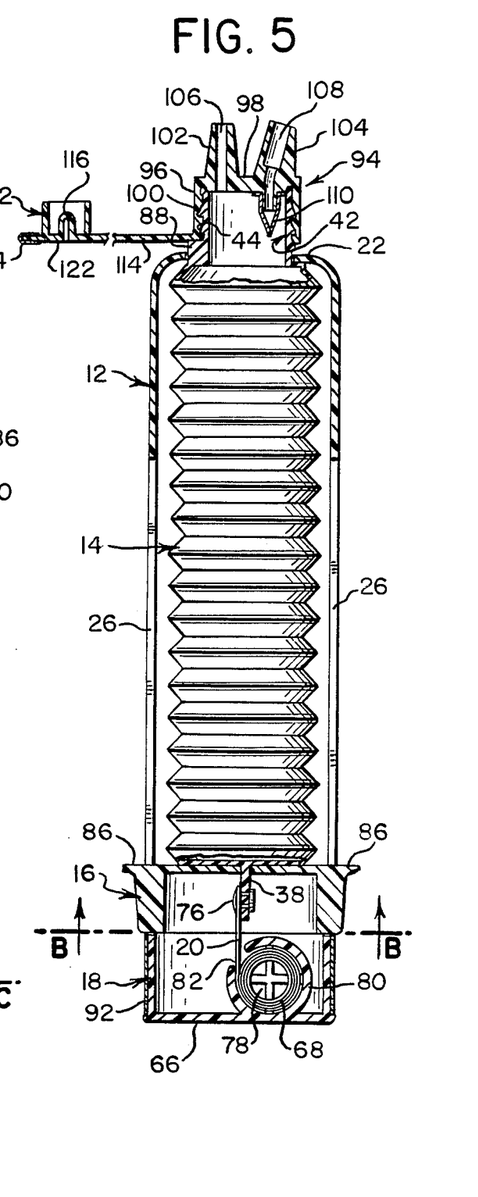
FIG. 5 is a side elevational view partially in cross-section of the device of FIG. 1 taken in the direction of line A—A of FIG. 1.

FIGS. 1, 4 and 5 also illustrate an alternative embodiment of the housing 12, bellows 14, slide collar 16 and the base 18. The cross bar 48 is not employed and in its place the collar ring 46 has an upper end 74 which has an opening of suitable dimension to snugly receive the appendage 38 of the bellows 14 in a tight fitting relationship. As shown more clearly in FIG. 5 the bellows 14 and spring free end 70 are attached together underneath the upper end 74. An eyelet 76 can be used instead of the nut 56 and bolt 54 arrangement shown in FIG. 2. The eyelet 76 is suitably dimensioned so that it can be press fitted through opening 40 in appendage 38 of the bellows 14 and the opening in the spring free end 70. The force supplied by the spring assembly 20 maintains the bellows 14 and the spring free end 70 in a fixed relationship with respect to the slide collar 16. The opening of the upper end 74 is smaller dimensionally than the combined width of the spring free end 70 and appendage 38 so that the latter cannot pass therethrough when coupled to the spring free end 70.

According to the embodiment illustrated in FIGS. 1, 4 and 5, the coiled spring portion 68 can be kept coiled within a pocket 78 defined within an annular wall 80 formed integrally with the bottom end wall 66. The free portion 70 of spring assembly 20 passes through an opening 82 formed in annular wall 80. As also shown in FIGS. 4 and 5 the bottom end wall 66 is integrally formed both with the base 18 and housing 12 in two halves joined at seam 84 as shown in FIG. 1. The tabs 50 according to FIG. 1 have an outwardly projecting member 86 against which the user's fingers can rest in order to aid in compressing the bellows.

The tube 42 as shown in FIG. 5 is secured to the upper end wall 22 by a key shaped member 88 which passes through a like dimensioned notch in the upper end wall 22. By slightly twisting the key shaped member 88, the tube 42 is locked in place.

The assembly of the device 10 may be finalized by the bonding of separate structural components together. In the embodiment of FIG. 2, preferably the ring 30 of the other end of housing 12 is glued into the groove 72 on the upperside of the integral base top end wall 60. The cross bar 48 can also be glued into its cutouts (not shown) in the collar ring 46 of slide collar 16. Alternatively, the end walls 22 and 60, and tube 42 can be constructed separately from their respective structures and glued thereto. In a preferred assembly, ultrasonic welding is used to attach the ring 30 to the groove 72. Assembly of the device 10 is not limited to gluing and ultrasonic welding but may be accomplished by any other conventional means known and appreciated by those skilled in such arts including but not limited to mechanical means such as screws. Similarly, the embodiment of FIG. 1 can be assembled by installing the bellows 14 and spring assembly 20 within one half of the integral housing 12 and base 18 and thereafter securing the second half thereto along seam 84.

Preferably the housing 12 will be made of a transparent plastic and will have etched graduations 90 thereon as shown in FIGS. 1 and 2. The user will therefore be able to visibly inspect the proper operation of the device 10. Additionally he can measure the amount of fluid collected upon holding the bellows upper end 32 upside down and comparing the fluid level against the graduations 90.

The device 10 can be supplied with a protective wrapping (not shown) to prevent inadvertent release of tabs 50 from their locked position when the device 10 is prepared and distributed in a preactivated state. The wrapping can also serve to provide user or other desired information printed thereon. Additionally information may be imprinted on the base botton end wall 66 by the user to identify the patient and other pertinent data relevant to the particular usage of the device 10. Instructional or user information may also be placed or written on band wrapper 92 positioned about the base 18 as shown in FIG. 1. Yet other information may also be provided by means of decals, etching, frosting or texturing upon the outer surface of housing 12 as in the space identified as "D" in FIG. 1.

Preferably the bellows 14, base 18, slide collar 16 and tube 42 are made by injection molding of suitable plastic material.

Advantageously the housing 12 is substantially rigid thereby avoiding the possibility of inadvertent compression by a patient rolling over onto the device 10.

The bellows tube 42 can be supplied, if desired, with a cap 94 as shown in FIGS. 1, 4 and 5. The cap 94 preferably has a cylindrical side wall 96 and an upper end wall 98. The inside of the cylindrical side wall 96 has ledges 100 which cooperate with the flanges 44 of the tube 42 as shown in FIG. 5 so that the cap 94 may be positioned in a secure fashion over the tube 42. The upper end wall 98 has two upstanding tabular projections 102 and 104 which form ducts 106 and 108, respectively. The projection 104 also extends beneath the undersurface of end wall 98 to accomodate a one-way Vernay valve 110 placed thereover. Also provided with the cap 94 is a cap seal 112 connected to the side wall 96 by a strand 114. The cap seal 112 is configured to sealingly seat upon the outer end of projection 102. To aid in this sealing, the cap seal 112 has an internal nipple 116 configured and dimensioned so as to be sealingly inserted within duct 106 when seal cap 112 is positioned over projection 102. The inside of duct 108 is configured and dimensioned to receive wound tubing 118 inserted therein as shown in FIG. 1. In this fashion, the tube 42 can be covered at its outer end by the cap to maintain a sterile environment within the bellows 14 prior to use or to seal the fluids within the bellows 14 during and after use.

In normal operation or usage, the duct 106 is sealed with seal cap 112 so that fluid from a wound may enter the bellows 14 through tubing 118, duct 108 and one-way valve 110 which prevents any fluid within the bellows 14 from returning to the wound.

Figures 3, 6, 7, 8:
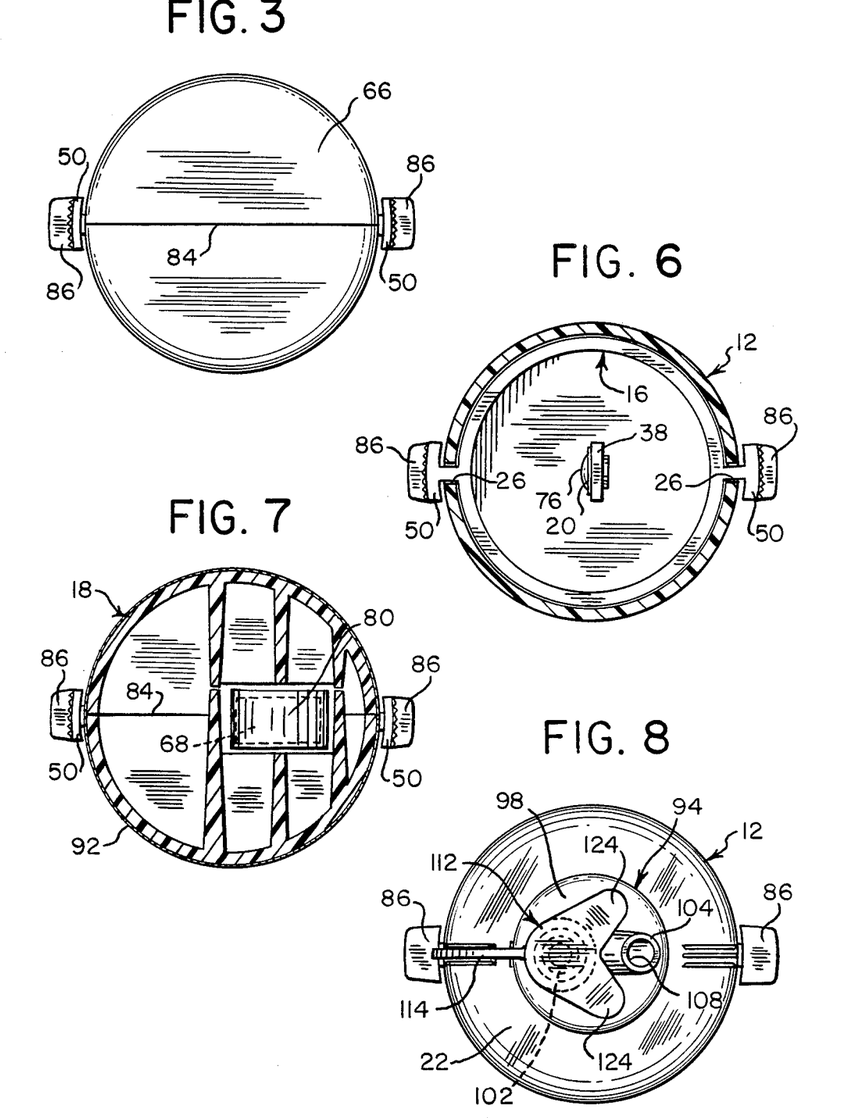
FIG. 3 is an end view of the device of FIG. 1 taken in the direction of arrow "A".
FIG. 6 is a view of the device of FIG. 1 taken along line B—B in FIG. 5.
FIG. 7 is a view of the device of FIG. 1 taken along line C—C in FIG. 4.
FIG. 8 is a top view of the device of FIG. 1.
Figure 9:
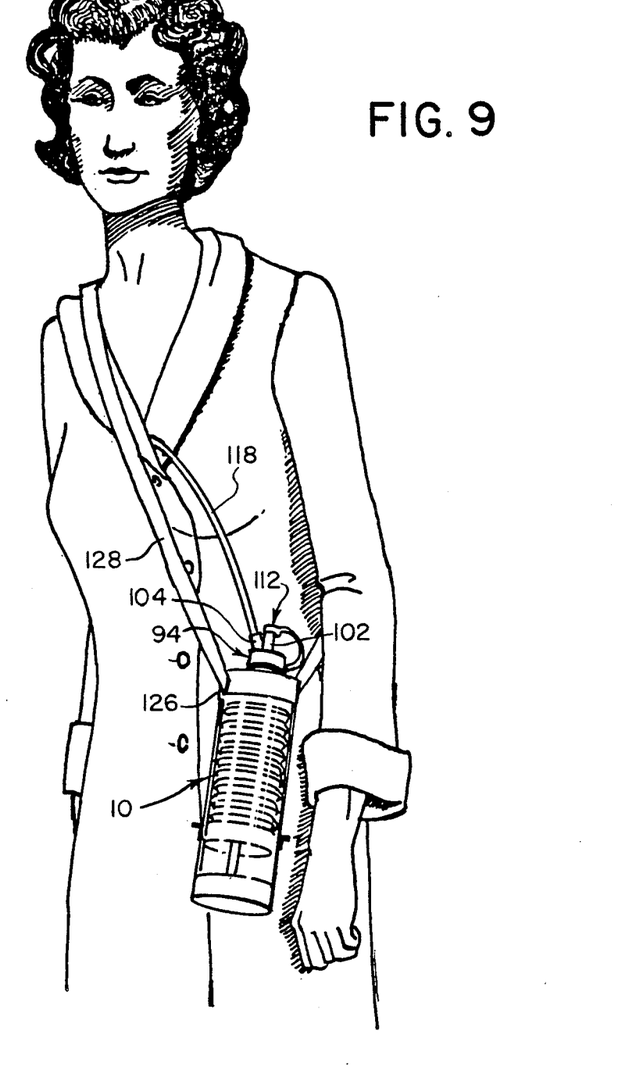
FIG. 9 illustrates a wound drainage device in use as portably worn by a patient.

If desired, the cap seal 112 may be removed and fluid within the bellows 14 may be drawn or expelled therefrom through duct 106 for immediate testing or diagnosis in a pathology laboratory. In a similar fashion, the bellows 14 may be completely evacuated, if desired, for immediate reuse. A retainer clip 120 as shown in FIG. 1 is provided on housing end wall 22 to hold the strand 114 and cap seal 112 in place during the evacuation procedure described above. Cap seal 112 is provided with an arrow-shaped top wall 122 with extending legs 124 as shown more clearly in FIG. 8 which facilitate the grasping and removal of the cap seal 112. To aid in securing the suction device 10 to the patient, the housing 20 has an integral C-clip 126 as shown in FIG. 1 which accommodates a strap 128 positioned about the patient as shown in FIG. 9. In this manner, the device 10 can be portably supported from the patient without the need for any other support structure.

The bellows tube 42 can alternatively be supplied, if desired, with a conventional Y connector (not shown). One duct of the conventional Y connector would be secured to the tube 42. Another duct would be connected via conventional urethane tubing to an additional Y connector (not shown) which would also be connected to wound tubing (not shown) having one end disposed in the wound. A conventional non-return valve (not shown) could be inserted at some position along the tubing configuration. The remaining duct of the Y connector connected to the tube 42 would have a cap (not shown) arranged similarly to cap 94 for tube 42. Normally this cap would seal the remaining duct while fluid is drawn from the wound through the conventional tubing and into the bellows 14. However, removal of the cap on the remaining Y connector duct permits evacuation of fluid from the bellows 14 by advancing the tabs 50 toward the first position ("B") thereby compressing the bellows 14. Thus the fluid may be totally evacuated from the bellows 14 which then is ready for continued use. Alternatively, the bellows 14 can be partially evacuated into another container to permit immediate transfer of the fluid for study, e.g., in a pathology laboratory, without disrupting the hookup of the device 10 for further removal of fluid from a wound or the like.

The device 10 is economically designed to permit either discarding of the entire unit, or reuse after evacuating the fluids therein. If desired, the bellows 14 after complete evacuation may be cleansed and reactivated for further use by means of the Y connector via the discharge procedure described above.

In the preferred embodiment, the spring assembly 20 is a programmed variable force ribbon spring as shown in the FIGS. and as disclosed and illustrated in U.S. Pat. Nos. 2,609,191; 2,609,192; and 2,609,193. The variable force ribbon spring is programmed so that the combined restoring resultant force of the variable forces produced by the expansion of the bellows 14 and the contraction of the ribbon spring produces a substantially constant force of expansion. The variable force produced by the bellows 14 complements the variable programmed force produced by the contraction of the ribbon spring. In this manner, the device 10 provides a substantially constant suction throughout the range of evacuation, a feature found generally by most doctors and other medical personnel to be quite desirable in such devices. Furthermore, such spring and resulting force assemblies render the device 10 generally insensitive to orientation so that no particular orientation of the device 10 is required. In addition, the operation of the device 10 is insensitive as well to the amount of fluid already collected within the bellows 14.

Other embodiments according to the present invention are possible with a programmed variable force means other than the spring assembly 20 as disclosed. Moreover, various structural configurations are possible without departing from the scope of the invention. In this respect, the bellows 14 can be fixed at the lower end of the housing 12 and permitted to expand towards the housing end wall 22 with suitable tubing and force means provided therewith. Also, the various alternative embodiments of the housing 12, base 18 and collar 16 can be interchanged with each other to obtain various alternative configurations without departing from the teaching of applicants' invention.

We claim:

1. A device for drawing fluids therein comprising:
   a. a housing having an end wall and an opening therein;
   b. an airtight and watertight resilient container disposed within the housing and being collapsible and expandable therein;
   c. means for communicating with the interior of the container;
   d. means for collapsing the container within the housing; and
   e. variable force means for automatically expanding the container from its collapsed state such that the combined resultant force of the variable forces provided by the container and the variable force expansion means allows for the creation of a substantially constant level of negative pressure within the container so as to provide for the drawing of fluids therein at a substantially constant level of suction, said variable force expansion means being disposed outside the container.

2. The device according to claim 1 wherein the variable force expansion means is a variable force spring assembly disposed outside the container and secured to the housing and the container.

3. The device according to claim 2 further including means for retaining the container in a collapsed state.

4. A device for removal of fluids from a wound comprising:
   a. an elongated housing having at least one end wall at one end thereof, said end wall having an opening;
   b. an airtight and watertight resilient elongated bellows disposed within the housing, the bellows being collapsible and expandable and having an upper and a lower end;
   c. means for communicating with the interior of the bellows;
   d. means for maintaining the upper end of the bellows adjacent said end wall of the housing;
   e. means for collapsing the bellows within the housing; and
   f. variable force means for automatically expanding the bellows from its collapsed state such that the combined resultant force of the variable forces provided by the bellows and the variable force expansion means allows for the creation of a substantially constant level of negative pressure within the bellows so as to provide for the removal of fluids from the wound at a substantially constant level of suction substantially throughout the range of evacuation, said variable force expansion means being disposed outside the container.

5. The device according to claim 4 wherein the variable force expansion means is a variable force spring assembly.

6. The device according to claim 5 further comprising means for retaining the bellows in a collapsed state.

7. The device according to claim 6 further comprising a base capable of being mated and attached to the other end of the housing, one end of said variable force spring assembly being secured within said base.

8. The device according to claim 7 wherein the housing has a side wall of a generally cylindrical configuration.

9. The device according to claim 8 further including at least one slit of suitable width, said slit disposed in the side wall of the housing and aligned with the longitudinal axis of the housing, said slit extending from a first position spaced from the end wall to a second position spaced from the other end of the housing.

10. The device according to claim 9 wherein the collapsing means comprises a disc-shaped collar slidably engaged within the housing between the other end of the housing and the lower end of the bellows and secured to the other end of the variable force spring assembly, said collar being attached to the lower end of the bellows, said collar having extending radially therefrom at least one tab, said tab being slidably engaged within and extending beyond said slit, whereby movement of said tab toward the first position collapses the bellows.

11. The device according to claim 10 wherein the first position is suitably chosen so that the bellows is substantially fully collapsed when said tab is at the first position.

12. The device according to claim 11 wherein the retaining means comprises at least one cutout positioned at the first position and communicating with said slit, said cutout suitably dimensioned and configured so as to receive said tab when said tab is at the first position and twisted into the cutout such that said cutout retains the tab and retains the bellows in a collapsed state.

13. The device according to claim 12 wherein said variable force spring assembly is a ribbon spring having a free end extending along the longitudinal axis of the housing and being attached to the bellows, such that release of said tab from its cutout allows the ribbon spring to draw the collar toward the other end of the housing so as to expand the bellows and produce a negative pressure therein.

14. The device of claim 13 wherein the housing is substantially rigid.

15. The device according to claim 14 wherein the housing is a transparent plastic so as to permit visible inspection of the operation of the bellows, the collar, and the ribbon spring within the housing.

16. The device according to claim 15 wherein the bellows is a transparent plastic thereby permitting the visible inspection of the fluid withdrawn therein from the wound.

17. The device according to claim 16 further including graduations disposed on the housing so as to permit the measuring of fluid withdrawn therein from the wound.

18. The device according to claim 16 further including a predetermined area on the housing which is textured so as to permit selective imprinting of desired information thereon.

19. The device according to claim 18 wherein said textured area is frosted.

20. The device according to claim 4 wherein the communicating means includes a hollow tube, said tube being integral with the upper end of the bellows and extending through the opening of said end wall such that the interior of the bellows is in communication with the outside of the housing.

21. The device according to claim 20 wherein the maintaining means includes a partial flange disposed on the hollow tube and above the upper end of the bellows a distance at least slightly larger than the thickness of said end wall, said flange adapted to normally permit one-way passage of the hollow tube from within to without the housing through the opening of said end wall such that the upper end of the bellows is maintained adjacent said end wall of the housing.

22. The device according to claim 20 wherein said end wall has a second opening therethrough.

23. The device according to claim 22 wherein the bellows includes an integral member extending outwardly from said end wall, the integral member being dimensioned and configured so as to pass through the second opening from within to without the housing such that the upper end of the bellows is maintained in a secured relationship with said end wall of the housing.

24. A device for drawing fluids from a portion of a human body comprising:
  a. a housing having at least one opening;
  b. airtight and watertight resilient container means disposed within the housing, the resilient container means being collapsible and expandable and having its interior in communication with the opening in the housing;
  c. variable force expansion means disposed outside the resilient container means and secured to the housing for automatically expanding the resilient container means from at least a partially collapsed state such that the combined resultant force of the variable forces provided by the resilient container means and the variable force expansion means allows for the creation of a substantially constant level of negative pressure within the resilient container means so as to provide for the drawing of fluids therein from the portion of a body at a substantially constant level of suction substantially throughout the range of evacuation; and
  d. means for connecting the opening of the housing to the portion of the body so that fluids may be drawn therefrom into the interior of the bellows.

25. The device according to claim 24 further including means for portably supporting the housing from the body.

26. A method for drawing fluids from a portion of a body comprising:
  a. taking a suction device in a preactivated state, said device including a housing having at least one opening, airtight and watertight resilient container means disposed within the housing, the resilient container means being collapsible and expandable and having its interior in communication with the opening in the housing, and variable force expansion means disposed outside the resilient container means and secured to the housing for automatically expanding the resilient container means from at least a partially collapsed state such that the combined resultant force of the variable forces provided by the resilient container means and the variable force expansion means allows for the creation of a substantially constant level of negative pressure within the resilient container means so as to provide for the drawing of fluids therein from a portion of a body at a substantially constant level of suction substantially throughout the range of evacuation;
  b. connecting the opening of the housing to a portion of a body from which fluids are to be drawn; and
  c. activating said suction device so as to draw fluids into said suction device at said substantially constant rate of suction.

27. The method according to claim 26 further including portably supporting said suction device from the body so as to permit the body to move about without any need for support of said suction device independent of the body.

* * * * *